(12) United States Patent
Pressman et al.

(10) Patent No.: US 6,430,309 B1
(45) Date of Patent: Aug. 6, 2002

(54) SPECIMEN PREVIEW AND INSPECTION SYSTEM

(75) Inventors: Norman J. Pressman, Glencoe; Richard A. Domanik, Libertyville, both of IL (US)

(73) Assignee: Monogen, Inc., Vernon Hills, IL (US)

( * ) Notice: Subject to any disclaimer, the term of this patent is extended or adjusted under 35 U.S.C. 154(b) by 0 days.

(21) Appl. No.: 09/034,690

(22) Filed: Mar. 4, 1998

Related U.S. Application Data

(63) Continuation of application No. 08/948,184, filed on Oct. 9, 1997, now abandoned, and a continuation-in-part of application No. 08/529,220, filed on Sep. 15, 1995, now abandoned, and a continuation-in-part of application No. 08/736,790, filed on Oct. 25, 1996, now Pat. No. 6,091,842, and a continuation-in-part of application No. 08/895,756, filed on Jul. 17, 1997, now Pat. No. 6,148,096.

(51) Int. Cl.[7] .................................................. G06K 9/00
(52) U.S. Cl. ........................ 382/133; 128/920; 378/43
(58) Field of Search ............................... 382/128–134, 382/173, 181, 214, 215, 224, 225, 227, 228; 348/79; 378/43; 128/920; 600/309, 368; 283/62; 435/6; 706/16

(56) References Cited

U.S. PATENT DOCUMENTS

| 3,824,402 A | * | 7/1974 | Mullaney et al. ............ 250/565 |
| 4,097,845 A | * | 6/1978 | Bacus ........................... 382/134 |
| 4,404,683 A | | 9/1983 | Kobayashi et al. ........... 382/134 |
| 4,513,438 A | | 4/1985 | Graham et al. ............... 382/134 |
| 4,812,909 A | | 3/1989 | Yokobayashi et al. ....... 348/589 |
| 4,965,725 A | | 10/1990 | Rutenberg et al. ........... 382/224 |
| 5,068,906 A | | 11/1991 | Kosaka .......................... 382/133 |
| 5,257,182 A | | 10/1993 | Luck et al. .................... 382/224 |
| 5,287,272 A | | 2/1994 | Rutenberg et al. ........... 382/224 |
| 5,528,703 A | | 6/1996 | Lee ................................ 382/257 |
| 5,544,650 A | | 8/1996 | Boon et al. .................... 600/309 |
| 5,548,661 A | | 8/1996 | Price et al. .................... 382/133 |
| 5,625,705 A | | 4/1997 | Recht ............................ 382/128 |

(List continued on next page.)

FOREIGN PATENT DOCUMENTS

| DE | 30 40 245 A1 | 8/1981 |
| DE | 33 13 789 A1 | 10/1983 |
| EP | 0 647 844 A2 | 4/1995 |
| WO | WO9106911 | 5/1991 |
| WO | WO9115826 | 10/1991 |
| WO | WO 95/02204 | 1/1995 |
| WO | WO9522749 | 8/1995 |
| WO | WO9603709 | 2/1996 |
| WO | WO 97/25678 | 7/1997 |

OTHER PUBLICATIONS

International Search Report in PCT/US98/14714, dated Oct. 27, 1998.
International Search Report in PCT/US98/14719, dated Oct. 27, 1998.
Neuromedical Systems, Inc. web page http://www.papnet.com dated May 28, 1997.
AcCell™ –Savant A cellular DNA analysis system, AccuMed International, Inc. 1997 (brochure).

*Primary Examiner*—Jayanti K. Patel
(74) *Attorney, Agent, or Firm*—Foley & Lardner

(57) ABSTRACT

A specimen preview and inspection system is disclosed. The system beneficially includes a preview stage, which provides a set of biasing-information for preview by a technician before the technician formally screens the specimen. The preview stage enables the technician to conveniently review information pertinent to the specimen at issue. The preview stage may thereby bias, or channel, the technician's attention during screening toward diagnostically significant aspects of the specimen. The invention is particularly useful in the context of Pap smear screening, although the invention may extend to inspection of other types of specimens or samples as well.

13 Claims, 11 Drawing Sheets

U.S. PATENT DOCUMENTS

| | | |
|---|---|---|
| 5,627,908 A | 5/1997 | Lee et al. .................... 382/133 |
| 5,655,029 A | 8/1997 | Rutenberg et al. .......... 382/133 |
| 5,671,288 A | 9/1997 | Wilhelm et al. ............. 382/128 |
| 5,677,966 A | 10/1997 | Doerrer et al. ............. 382/128 |
| 5,710,842 A | 1/1998 | Lee ............................. 382/283 |
| 5,715,326 A | 2/1998 | Ortyn et al. ................. 382/128 |
| 5,715,327 A | 2/1998 | Wilhelm et al. ............. 382/128 |
| 5,733,721 A * | 3/1998 | Hemstreet, III et al. ........ 435/6 |
| 5,740,269 A | 4/1998 | Oh et al. ..................... 382/133 |
| 5,745,601 A | 4/1998 | Lee et al. .................... 382/225 |
| 5,757,954 A | 5/1998 | Kuan et al. .................. 382/133 |

* cited by examiner

SPECIMEN PREVIEW AND INSPECTION SYSTEM

RELATED APPLICATIONS

This is a continuation of application Ser. No. 08/948,184, filed Oct. 19, 1997, now abandoned.

The present application is a continuation-in-part of the following U.S. patent applications, of which the entire disclosures are expressly incorporated herein by reference:

U.S. patent application Ser. No. 08/529,220, filed Sep. 15, 1995 and entitled "Cytological Specimen Analysis System with Individualized Patient Data," which names Vladimir Dadeshidze, Richard A. Domanik, Peter G. Gombrich and Lars J. Olsson as inventors, now abandoned.

U.S. patent application Ser. No. 08/736,790, filed Oct. 25, 1996 and entitled "Cytological Specimen Analysis System with Prescreening and Generation of Viewing Path Information," which names Richard A. Domanik and Vladimir Dadeshidze and Lars J. Olsson as inventors, now U.S. Pat. No. 6,148,842.

U.S. patent application Ser. No. 08/895,756, filed Jul. 17, 1997 and entitled "Specimen Preview and Inspection System," which names Norman J. Pressman and Richard A. Domanik as inventors, now U.S. Pat. No. 6,148,096.

The subject matter of the present application is further related to the subject matter disclosed in the following U.S. patent applications, each of which is also expressly incorporated herein by reference:

U.S. patent applications Ser. No. 08/529,188, filed Sep. 15, 1995 and entitled "System for Simplifying the Implementation of Specified Functions," which names Richard A. Domanik, Dennis W. Gruber and William J. Mayer as inventors.

U.S. patent application Ser. No. 08/529,198, filed Sep. 15, 1995 and entitled "Multifunctional Control Unit for a Microscope", which names Richard A. Domanik, Dennis W. Gruber, Peter G. Gombrich and William J. Mayer as inventors.

U.S. patent application Ser. No. 08/528,789, filed Sep. 15, 1995 and entitled "Automated Specimen Handling System and Method for Sorting the Specimens," which names Richard A. Domanik, Peter G. Gombrich, Dennis W. Gruber and William J. Mayer as inventors.

U.S. patent application Ser. No. 08/528,793, filed Sep. 15, 1995 and entitled "Specimen Management System," which names Richard A. Domanik, Peter G. Gombrich and William J. Mayer as inventors.

U.S. patent application Ser. No. 08/768,711, filed Dec. 18, 1996 and entitled "Multifunctional Control Unit for a Microscope," which names Richard A. Domanik, Dennis W. Gruber, Peter G. Gombrich and William J. Mayer as inventors.

BACKGROUND OF THE INVENTION

The present invention relates to specimen or sample inspection systems and more particularly to systems in which human operators inspect a substantial number of individual specimens to locate a particular subset such as "suspicious" or irregular specimens. As used herein, the term "specimen" is not necessarily limited to a medical or biological specimen but may more generally extend to any sample item or portion of a group as a whole.

The present invention may find particular use in a variety of contexts such as, for example, examining histological speciment (i.e., tissue-based as in anatomic pathology), examining cytological specimens (i.e., cellular samples (such as those taken from body cavity fluids, voided urine, sputum, and gynecological tract) as analyzed by cytotechnologists and cytopathologists, cytogeneticists, hematologists, neuroscientists, etc.), examining silicon wafers in an integrated circuit manufacturing process, and other materials inspection processes. In a typical scenario, a human inspector must inspect and analyze a substantial number of specimens each day to determine whether the specimens divert from some predetermined norm. Abnormal specimens are identified and are subject to further, more detailed review. The subsequent, more detailed review may require a reviewer with additional expertise, such as a pathologist in the case of the Pap test. In a usual case, most of the specimens are considered "normal," or "within normal limits," and therefore need not be rejected or subject to additional scrutiny. Depending on the detail and scope of this inspection and analysis, this additional scrutiny can unfortunately be a very slow, painstaking and costly process.

For purposes of illustration, the present invention will be described in the context of cytological specimen analysis, such as cervical Pap smear analysis. Pap smears, which are routinely taken from women, facilitate the detection of pre-cancerous changes and/or the early stages of cancer, thus reducing the chances of any cancer or related abnormal condition from spreading or advancing with the resultant negative impact on the prognosis for the patient. A Pap smear is prepared by first collecting a vaginal, cervical and endocervical tissue sample from a patient. The sample is then fixed to a slide, for instance by alcohol fixation, and Pap-stained to enable microscopic analysis. Alternatively, rather than preparing a Pap smear, the specimen may take the form of a liquid-based or monolayer preparation, using instruments manufactured, for instance, by AutoCyte or Cytyc. In practice, the slide is then screened by a highly skilled technician ("cytotechnologist"), in an effort to identify possible cellular abnormalities in the o specimen and to determine the specimen adequacy. The cytotechnologist generates notes regarding each specimen deemed to have possible abnormalities. The cytotechnologist then provides the specimen slide, together with notes of his or her findings, to an expert pathologist (i.e., specialized physician) for further review and final specimen diagnosis.

To screen a Pap smear specimen, the cytotechnologist generally views the Pap smear slide containing the Pap smear through a microscope to detect the presence of cancer cells or cells exhibiting other abnormal conditions. Because a cancerous cell may appear in only one of thousands of locations in an otherwise normal-appearing specimen, however, the cytotechnologist must generally examine every area of the slide in order to make a valid (i.e., accurate) determination. Further, many portions of the specimen slide may contain no cells at all, but the cytotechnologist must examine even those areas to at least determine the absence of pertinent (i.e., diagnostically significant) material. Of course, this process of thoroughly screening a specimen for the presence of cancerous or abnormal cells is often laborious, error-prone and costly. Still, cytotechnologists have been known to examine more than 20,000 slides annually in an effort to classify specimens as within normal limits and to identify abnormalities and enable pathologists to diagnose Pap smear specimens. In many cases, this specimen review rate is driven in part by financial concerns such as competition based on the number of specimens analyzed.

Based on the cytotechnologist's primary review (i.e., screening) of the specimen, the cytotechnologist determines either that the specimen contains suspicious material such as pre-cancerous or cancer cells, or that the specimen is apparently within normal limits. Typically, statistically speaking, "suspicious" and "abnormal" specimens may account for approximately 5% to 10% of Pap smears in the United States, in laboratories that are screening asymptomate women. The remaining statistical 95% to 90% of the cases in turn are classified as apparently normal.

If a specimen contains even a single well preserved and well-stained cancer cell out of tens or hundreds of thousands of cells, the cytotechnologist should find the specimen to be suspicious, or atypical or abnormal. Failure to properly identify a specimen as abnormal during this screening process may be disastrous, as it may leave a cancer patient undetected and untreated and may ultimately lead to the death of the patient.

The cytotechnologist forwards all "suspicious," or "atypical" or "abnormal," specimens to a pathologist for detailed review and final diagnosis and "sign-out" in light of the cytotechnologists notes and findings. One of the pathologist's goals is to analyze the specimen at issue and determine based on medical expertise whether the specimen contains cancerous or pre-cancerous cells. In doing so, the pathologist must strive to minimize both false negative diagnoses and false positive diagnoses, as false negative diagnoses could leave cancer undetected, while false positive diagnoses could result in unnecessary or inappropriate, harmful and costly cancer treatment such as chemotherapy or the like.

Most of the specimens that the cytotechnologist deems to be "apparently normal" are classified as within normal limits, and the analysis of those specimens is completed. However, to minimize the possibility of false negatives in the screening process and to identify cytotechnologists that may have screening quality performance problems, at least some of those specimens should be subject to a secondary screening, or "re-screening," by a cytotechnologist. In the United States, at least 10% of these "apparently normal" specimens must be randomly selected and re-screened for quality assurance by a different cytotechnologist.

In addition, to further minimize false negatives during the Pap smear screening process, cytotechnologists must spend sufficient time screening each specimen slide. For this reason, legal regulations in some states in America restrict individual cytotechnologists to screening no more than 100 Pap smear slides in a single day. Other states provide even stricter limitations, such as a maximum of 80 slides per day. Assuming an average 7 hour work day, these regulations would have a typical cytotechnologist screening and classifying an average Pap smear slide in no more than 4.20 to 5.25 minutes.

Notwithstanding these maximum limitations, the average number of Pap smear slides screened per day by cytotechnologists in the United States is on the order of only 50 to 60, corresponding to cytotechnologists typically spending less than 7 to 8 minutes reviewing each slide in order to carefully determine whether any abnormal cells are present. Of course, as cytotechnologists spend more time screening each slide, they will theoretically make fewer false negative errors. At the same time, however, as cytotechnologists spend more time screening each slide, they will screen fewer slides each day, and the labor and cost of specimen screening will consequently rise.

A need therefore exists for a more efficient specimen screening system that minimizes the presence of false negative specimen classification errors while reducing the time required to analyze specimens accurately and to compile useful information about suspicious, atypical, or abnormal specimens for reference by diagnostic experts.

SUMMARY OF THE INVENTION

The present invention provides improved efficiency in specimen analysis by better managing information associated with the specimen at issue. In turn, the invention recognizes that a skilled technician or technologist need not serially review every area of a specimen on a glass microscope slide or other substrate to locate one or more areas that are suspicious or abnormal, as long as the technician is provided with useful information about the specimen. Further, the invention recognizes that useful information may arise from information derived before the screening process by manual or automated techniques, or from the screening process itself, even if not expressly noted by the screening technician.

The present invention introduces a preview stage into the specimen screening process. The preview stage enables the technician to conveniently review information pertinent to the specimen at issue. A preview processor collects, measures, assembles, stores, communicates, displays and manages a variety of useful information about the specimen for quick analysis by the technician. In the context of Pap smear screening, this information may include, for example, aspects of the patient's medical history and medical risk factors, information pertinent to the preparation of the specimen, information about other tests conducted on the specimen from samples derived from aliquots of the same specimen, and discrete images of the most suspect cells on the slide from the specimen. The technician can flag (i.e., electronically mark) any of the information that may bear on whether the specimen at issue is abnormal. In addition, the technician may view other related information to place the specimen in context, such as, for instance, comparing the specimen with other known specimens having similar characteristics. Such comparison may be visually based upon cell images, or may be based on a graphical plot, numerical data or textual descriptions.

Provided with this preview information, the technician can quickly form an educated opinion as to whether the specimen at issue is likely to be normal or is likely to be suspect. The technician then conducts an actual screening of the specimen, for instance, through an automated microscope keyed to an established routing function. Beneficially, if the technician has already determined from the preview stage that the specimen is likely to be normal, for instance, by finding no information suggesting the presence of abnormalities, either from prior data or from specific specimen-derived information, then the technician may accelerate the specimen-screening process and may quickly screen the specimen in less than currently average time. Alternatively, if the technician has determined that the specimen is likely to be of interest, for instance, by having noted or flagged suspicious cells or other significant information, then the technician may appropriately spend more than an average amount of time screening the specimen. The previewed information can also be used to "drive" the cytotechnologist to suspicious areas on the slide before the routine screening function begins.

Additionally, as the technician examines and flags pertinent information associated with the specimen at issue during the preview stage, this information may conveniently be stored in an electronic record together with the technician's notes, for subsequent review by a diagnosing expert.

This record may be associated with the specimen by a bar code or other identifying indicia. As the expert may also be provided with the coordinates identifying specific regions of the specimen referenced by the technician, the expert may beneficially associate the information flagged by the technician with specifically identified regions of the specimen.

In addition to including expressly flagged information in the record associated with each specimen, the invention may further include in the record useful information about the actual screening process automatically flagged by a computer-aided instrument that monitors the screener's behavior. For instance, in the event the technician spends a significant amount of time reviewing one particular area of the specimen, the invention may automatically include an indication in the record that the particular area may be of interest. In this way, even if the technician fails to expressly flag a region or expressly note the possible significance of a region of the specimen, the reviewing expert may be provided with useful information or hints about the region.

It is thus an object of the present invention to provide a prescreening system for specimen analysis. It is a further object of the present invention to provide a system for channeling a screening technician's interest and attention on specimens most likely to be suspect as well as the most suspect information about, and areas of, those specimens. Still further, it is an object of the present invention to provide a system for automatically compiling useful specimen-analysis information for subsequent review, based on information flagged by a screening technician and further based on the behavior of the screening technician. Yet further, an object of the present invention is to provide a specimen screening station that enables accurate, precise and robust analysis. Additionally, an object of the present invention is to provide a human screener with an apparatus and method to reduce screening times significantly for within normal-limit specimens (i.e., the most prevalent cases) without sacrificing diagnostic accuracy.

These, as well as other objects and advantages of the present invention will become readily apparent to those skilled in the art by reading the following detailed description, with appropriate reference to the accompanying drawings.

BRIEF DESCRIPTION OF THE DRAWINGS

A preferred embodiment of the present invention is described herein with reference to the accompanying drawings, in which.

DETAILED DESCRIPTION OF THE PREFERRED EMBODIMENT

Figure 1:
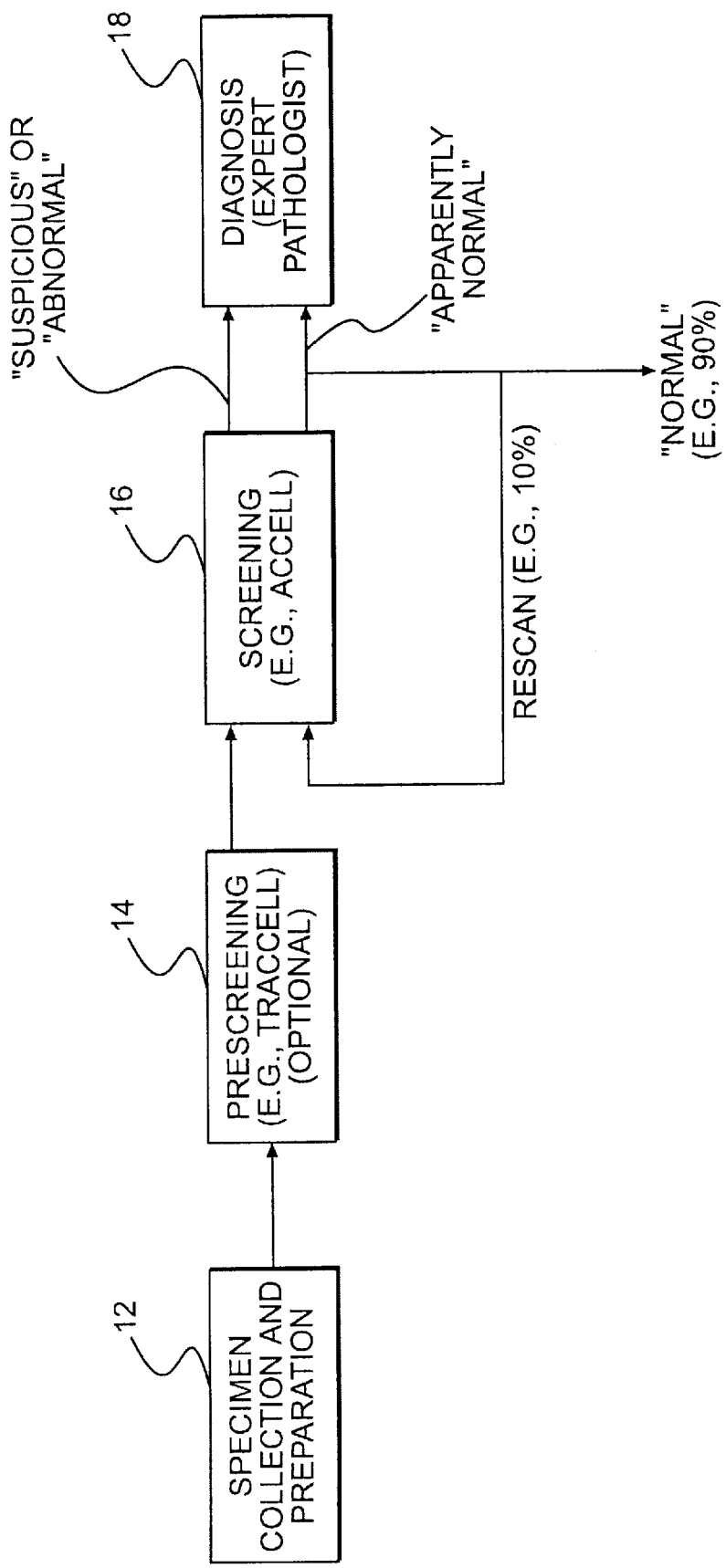
FIG. 1 is a block diagram illustrating the process flow in a preliminary embodiment of the present invention.

Referring to the drawings, FIG. 1 illustrates a block diagram of the system flow in a preliminary embodiment of the present invention. At block 12, a specimen is collected and prepared, for instance on a 1×3 inch slide with a 1×2 inch coverslipped area. At blocks 14 and 16, the specimen is then subjected to a cytological screening system, which includes automated machine prescreening and visual screening by a cytotechnologist. Based on the screening process, the cytotechnologist determines either that the specimen is suspicious or that the specimen appears to be normal. All specimens that are deemed suspicious are forwarded to an expert for review and diagnosis, at block 18. Of the specimens that are deemed to be apparently normal, at least 10% are re-screened at block 16 for quality control and particularly to reduce the possibility of false negatives.

Figure 2:
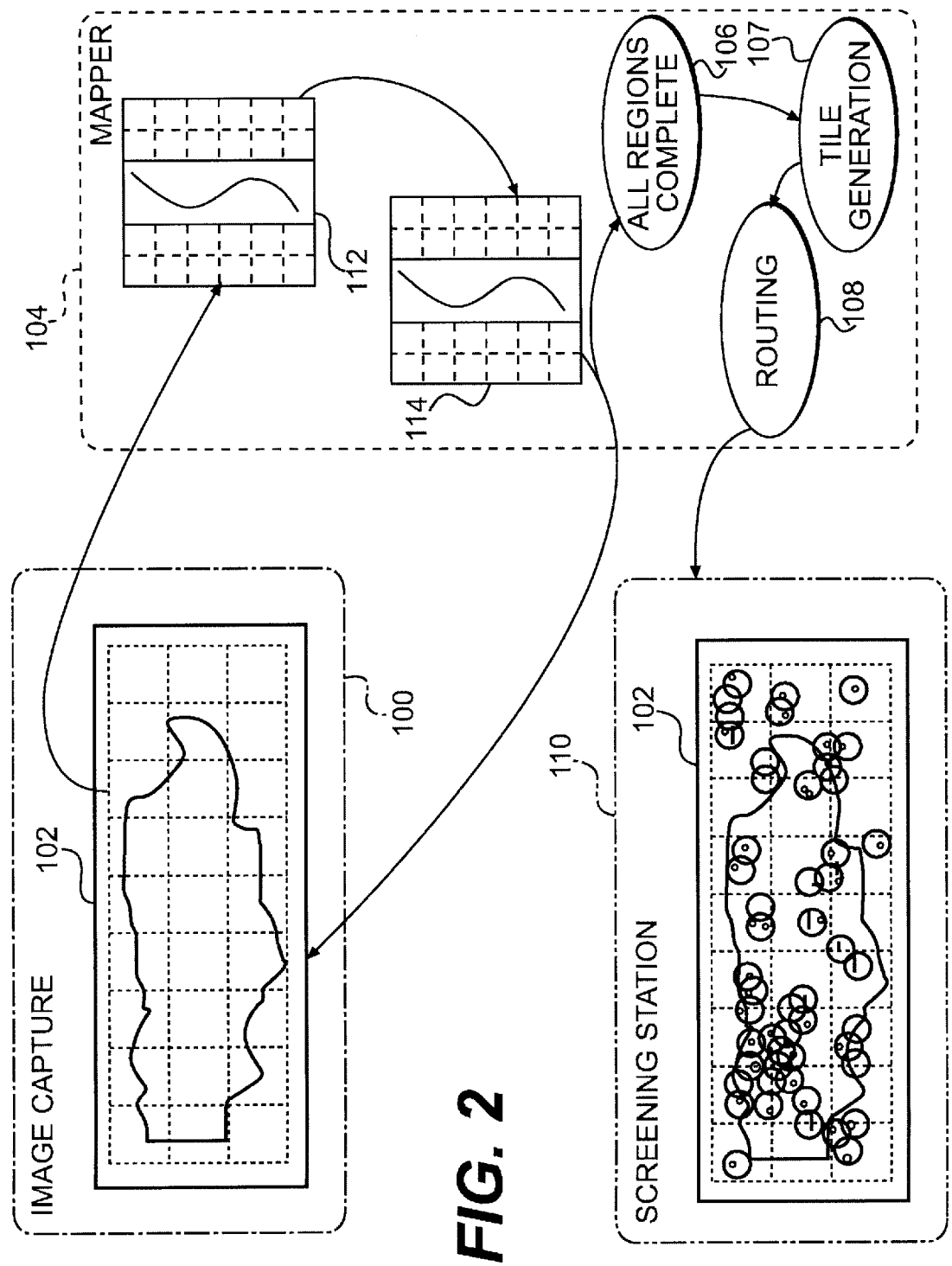
FIG. 2 is a flow diagram illustrating components employed and functions performed by a prescreening and screening system in the present invention.

FIG. 2 shows, by way of example, some of the functions that may be performed in the prescreening and screening stages 14, 16 of the present invention. In combination, these stages are adapted for use in a clinical laboratory or similar facility, and preferably include an image capture apparatus 100, a mapper 104 and an automated microscope-based screening station 110.

The image capture apparatus 100 preferably takes the form of a camera and a frame grabber. The camera is preferably a CCD (charge coupled device) scientific grade type camera with a 1K×1K or larger format, and a 3 class or better sensor. Such a camera is available commercially under the trade name ES-1 from Kodak Corporation, Rochester, N.Y., and is also available from Pulnix America, Sunnyvale, Calif. Such a camera is characterized by an active sensor area of 9 mm×9 mm or larger with a pixel spacing of 9 microns or finer and can capture, or scan, images at a rate of at least 30 frames/second and provide a digital output at a minimum rate of 30 MHz. The optical system is configured to provide an effective pixel resolution of approximately 2.4 microns at the sample. While such a resolution is appropriate for the preferred embodiment described herein, it may be changed for other applications. The specifications stated herein are illustrative of a particular preferred embodiment and may be altered. As an example, a camera with a format larger than 1K×1K would reduce the number of images to be captured, because each captured image would contain a larger portion of the slide. As another example, a pixel spacing of finer than 9 microns would result in higher resolution.

The camera provides its digital output to a frame grabber, which operates to store the digital data received from the camera. The frame grabber preferably employs a PCI type interface and is characterized by a data transfer rate of at least 50 MHz. In addition, the frame grabber preferably also employs digital signal processing for shading correction and blob finding. A preferred frame grabber takes the form of a Data Raptor type frame grabber available from Bit Flow Corp., Woburn, Mass. In an alternative embodiment, the frame grabber may perform certain image analysis and enhancement functions by way of specialized hardware devices, to provide a speed increase over performing such functions in software. For instance, the frame grabber may be configured with specialized hardware, such as digital signal processing circuitry, to perform some of the functions described below as being performed by software.

Image capture of a specimen on the slide 102 is performed by subdividing the slide into a plurality of equally sized regions, illustrated by the dotted lines in the slide 102, and individually capturing digital images of the specimen, region-by-region. The digital image of each region is stored in a memory once captured and is analyzed by the mapper 104. The regions of the slide shown in FIG. 2 are simplified for sake of illustration. In practice, a slide will typically have far more regions than shown in FIG. 2. For example, a typical slide that measures approximately 75 mm×25 mm, with an area of roughly 50 mm×25 mm being occupied by a specimen. Such a slide will contain regions of approximately 2.5 mm×2.5 mm, totaling approximately 200 regions for the slide.

In the preferred embodiment, the mapper 104 is implemented as a software program stored in a semiconductor, magnetic or other similar type of storage device and executed by a general purpose digital computer. One such slide-mapping system is the TRACCELL® system available from AccuMed International, Inc., of Chicago, Ill. The mapper 104 performs automated image analysis of the captured digital images. As an example, the mapper may operate to automatically analyze each region for the presence of cytological material. If any cytological material is detected, the region is designated by the mapper as a "screenable" region. As another example, the TRACCELL® system may be configured to make preliminary determinations about the specimen as a whole, such as whether the sample is adequate. Inadequate samples may then be identified and returned without further analysis.

Once all regions of the slide 102 have been captured and analyzed as indicated at block 106, the mapper 104 generates a plurality of tiles as indicated at block 107. For simplified illustration, these tiles are shown as circles within the slide 102 at the screening station 110. Each of the tiles may correspond to a field-of-view selected by the cytotechnologist for the microscope at the screening station. Collectively, the tiles surround all of the cytological material determined by the mapper to be required for viewing by the cytotechnologist. For this reason, as those of ordinary skill in the art will appreciate, other tiling shapes and configurations, such as hexagons, may alternatively be employed to further improve screening efficiency.

The mapper 104 assigns spatial slide coordinates to each tile or specimen region of interest and develops a routing function defining an optimal route for microscopic display of the designated specimen areas. The mapper then transmits the coordinates to the screening station 110. The screening station includes a microscope with a motorized stage and focus drive assembly, each of which may be operated by computer control or by an operator employing an ergonomic input device, or by a combination of computer and human control. The screening station is coupled to the mapper 104 via a serial link and, upon receiving a series of coordinates from the mapper, displays microscopic fields-of-view of the areas designated by the mapper in accordance with the routing function, or routing pattern, developed by the mapper.

Figure 3:
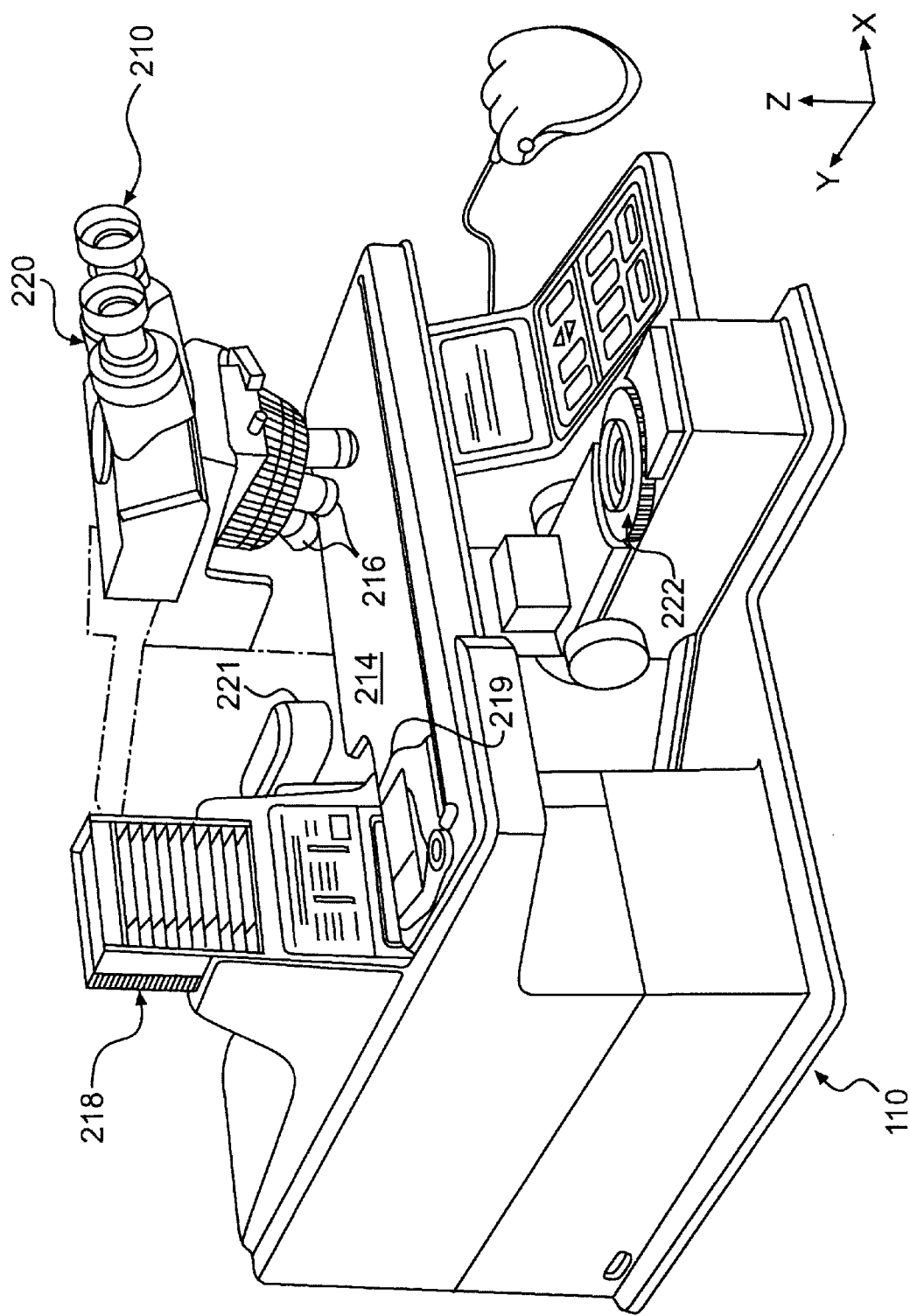
FIG. 3 is an illustration of a automated microscope-based screening station that may be employed in the present invention.

A preferred screening station is the ACCELL® specimen screening station produced by AccuMed International, Inc., of Chicago, Ill. FIG. 3 illustrates a preferred embodiment of this station 110, which includes an automated video microscope 210, to which a motorized stage 214, motorized focus driver (not shown) and motorized eyepiece 220 has been fitted. The automated video microscope 210 may be an Olympus BX-40 microscope, available from Olympus Optical Corporation of Tokyo, Japan and preferably includes a set of lenses 216 individually selectable by a motorized control. The screening station 110 includes a slide magazine 218, a slide holder 219, a bar code reader and printer 221, and a light source 222. The motorized stage 214 moves along an axis designated as the Y-axis in FIG. 3. In turn, slide holder 219 is connected to the motorized stage 214 and is itself motorized to move along an axis designated as the X-axis in FIG. 3. A controller board within station 110 receives external control signals to control the operation and movement of the motorized stage and slide holder, thereby providing automated movement of the specimen slide 102 in two dimensions relative to the microscope lens 216.

In the preferred embodiment, the camera of the image capture apparatus 100 is preferably affixed to a video port on top of the eyepieces 220 of the microscope 210, in order to capture cell images and avoid having to move the slide 102 between the microscope and the camera. The mapper 104 is in turn coupled to the screening station by way of a local area network. While neither the physical structure of the mapper and image capture apparatus or the manner of coupling the mapper to the screening station is critical, such an arrangement allows the mapper to be physically separate from the screening station and allows the mapper to transmit and receive information with a plurality of screening stations. Alternative arrangements of the manner in which the mapper and screening station are coupled, such as by way of example, a direct serial link, will be apparent to those of ordinary skill in the art in view of the present disclosure.

A cytotechnologist wishing to use the screening station 110 to view a slide inserts the slide or a group of slides into a slide carrier, which is then inserted into the slide magazine 218. The system extracts a slide from the magazine and scans a bar code on the slide using the bar code reader 221. The identity of the slide, as determined by the scanned bar code, is used by the system to retrieve coordinates from the mapper 104. The slide is then transported from the magazine onto the stage and positioned in accordance with the coordinates received from the mapper 104.

The cytotechnologist may set the speed at which he or she reviews these fields-of-view presented at the screening station 110. The cytotechnologist may, for instance, accelerate, decelerate or stop the automated review process. The mode of automated review can also be changed at will by the user. Such modes include, for example, stop-and-repeat screening, continuous screening, and slow-mode screening. Additionally, the cytotechnologist may at any time elect to switch to a manual review mode, for instance, in order to review surrounding areas on the slide at issue without being limited to the established routing pattern. Beneficially, the screening station 110 then enables the cytotechnologist to return to the automated routing pattern at the point that the cytotechnologist began to wander away from the established path. In this way, the station 110 helps to ensure that the cytotechnologist does not miss any areas of the specimen, including those that may be potentially critical to accurate diagnosis.

In a preferred embodiment, the screening system defined in part by the mapper 104 and the screening station 110 beneficially may be coupled to a database management system (DMS), for storage of information resulting from the screening process and in turn to facilitate passing pertinent findings to the expert pathologist for aid in diagnosis. The DMS preferably takes the form of a programmed general purpose desktop computer that has sufficient storage and processing capability to run a Microsoft Windows operating environment and an advanced database application such as Microsoft Access. When screening a specimen, the cytotechnologist may, for instance, enter notes about an area of the specimen, and those notes may be stored in the DMS together (in a database relationship) with the spatial coordinates of the area of interest, as provided by the mapper.

During subsequent diagnosis, the reviewing pathologist may conveniently access the notes corresponding to a specified slide or area of a slide by, for instance, scanning a bar code or other identifying code associated with the slide. In this way, once the specimen is passed to the pathologist for expert diagnosis, the pathologist may refer to the cytotechnologist's notes and the corresponding specimen region or regions of interest, which may be simultaneously or subsequently visualized.

Figure 4:
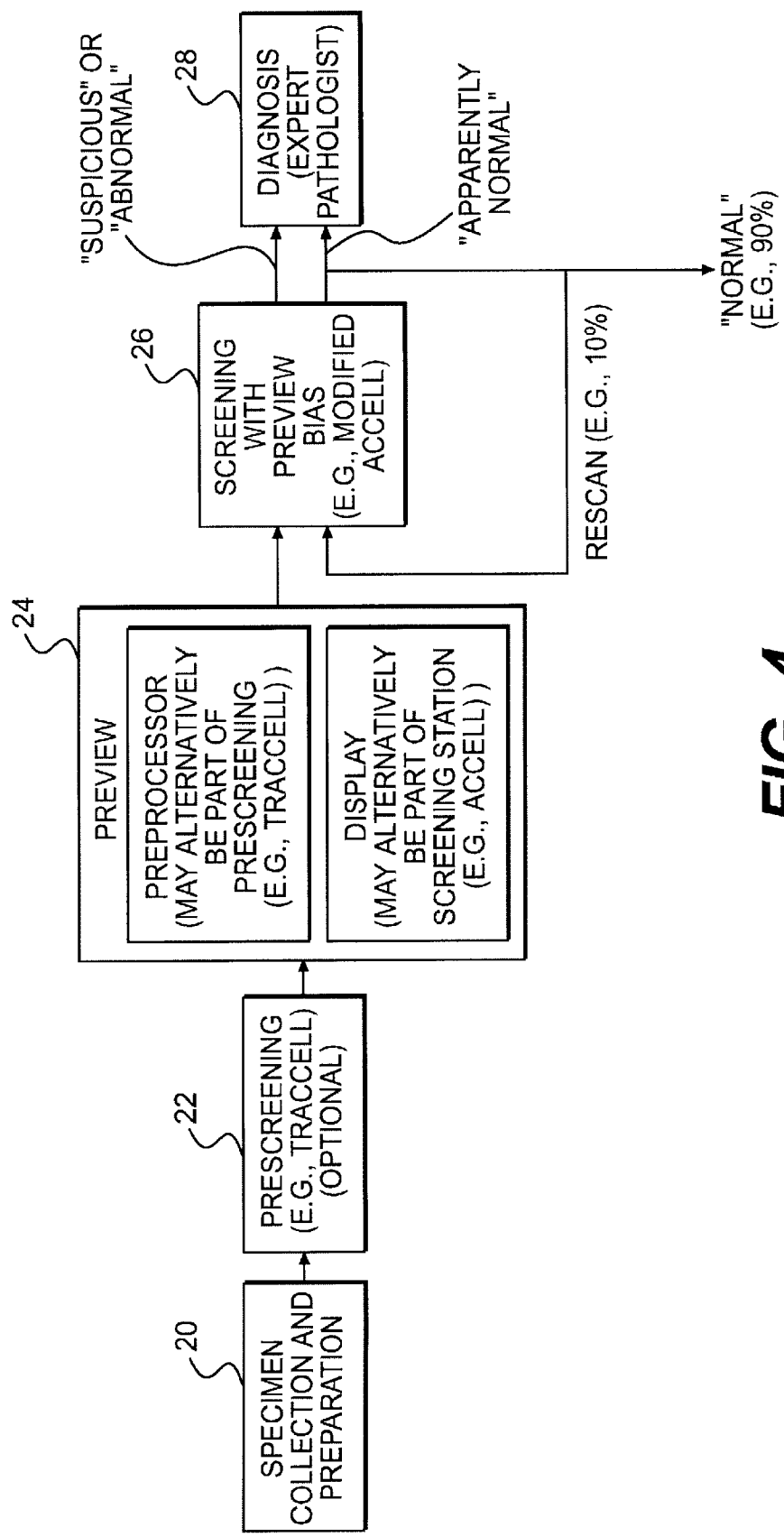
FIG. 4 is a block diagram illustrating the process flow in a preferred embodiment of the present invention.

FIG. 4 illustrates a block diagram of the system flow in an improved, preferred embodiment of the present invention. In FIG. 4, at block 20, a specimen is first collected and prepared. At block 22, the specimen is subjected to pre-screening by an image capture apparatus and a slide-mapper such as the TRACCELL® system. In the preferred embodiment, this automated prescreening process may be enhanced, as discussed further below.

Figure 8:
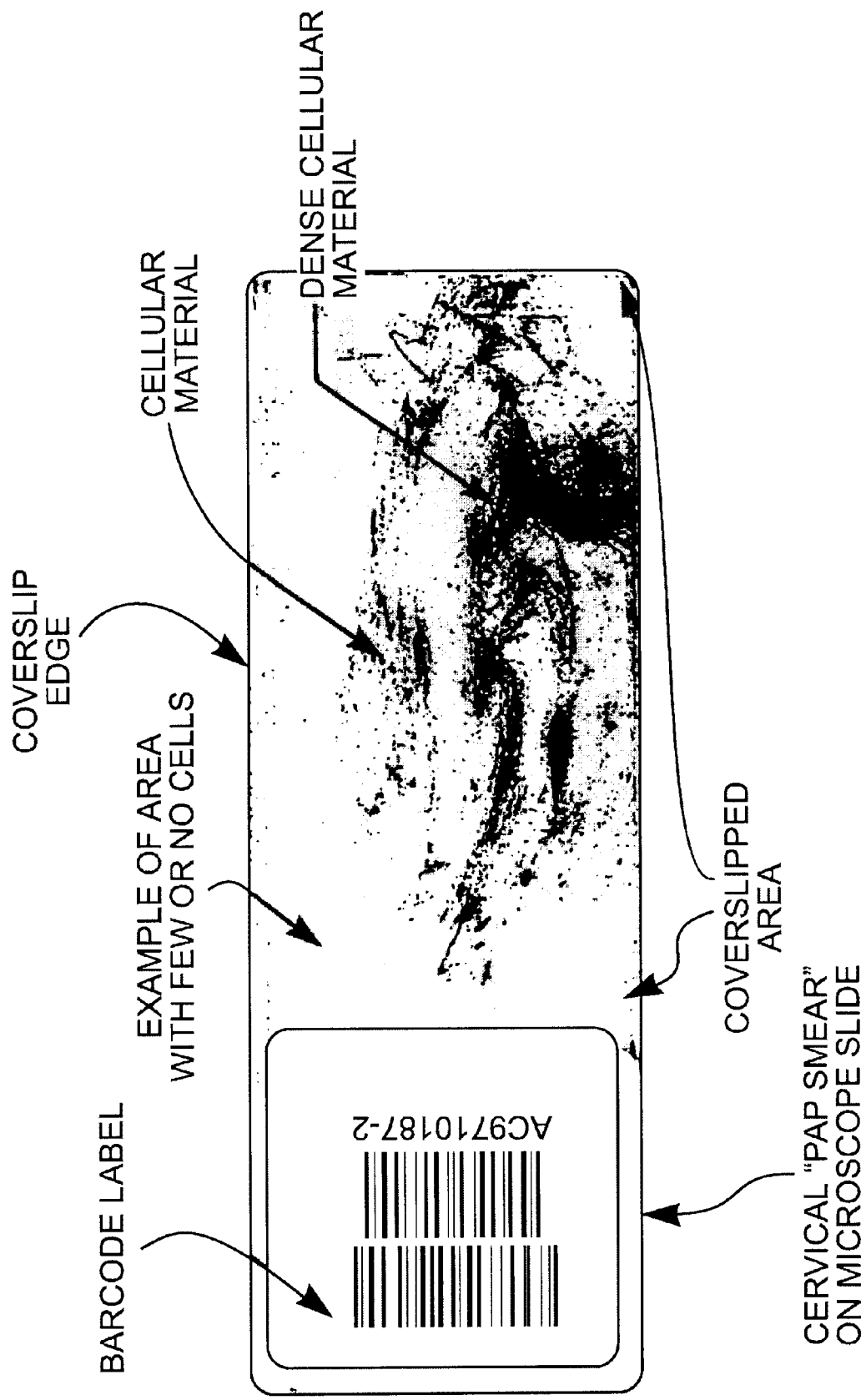
FIG. 8 is a graphical representation of a conventional "Pap Smear" cervical cytology slide.

Regarding specimen preparation, the conventional Pap smear process is limited because it produces large numbers of cells (50,000 to 300,000 cells per Pap smear, typically) that are often obscured by inflammatory materials that make accurate and sensitive diagnoses more difficult in some cases. The Pap smear process is also limited because it deposits the cells in a spatially non-uniform manner that is difficult and time-consuming to analyze visually, as shown, for example, by FIG. 8. Several alternative liquid-based sample preparation approaches have therefore been developed. One method depends upon centrifugation to separate cells before deposition onto a glass microscope slide, for example. Another method relies upon physical filtration of a specimen through a filter with a controlled pore-size distribution. An example of the latter approach is the Cytyc ThinPrep® instrument and process.

The Cytic ThinPrep® sample preparation generally comprises straining a sample through a filter having pores smaller than the average sample cell diameter but sufficiently large to allow passage of cellular and other debris. In one embodiment, the pore diameter is about 40–50$\mu$. The filter preferably has no rough edges or other features that would rupture the sample cells. Upon filtration, sample cells remain on the filter surface while the debris passes through, resulting in a filter surface enriched in sample cells and depleted in debris. The filter surface is next pressed onto a microscope slide to transfer the sample cells from the filter surface to the slide. This results in the slide having a monolayer of cells and, by employing a filter having a smaller area than the slide, a higher concentration of sample cells, substantially free of cellular and other debris that could interfere with a cytotechnologist's analysis of a slide.

Figure 9:
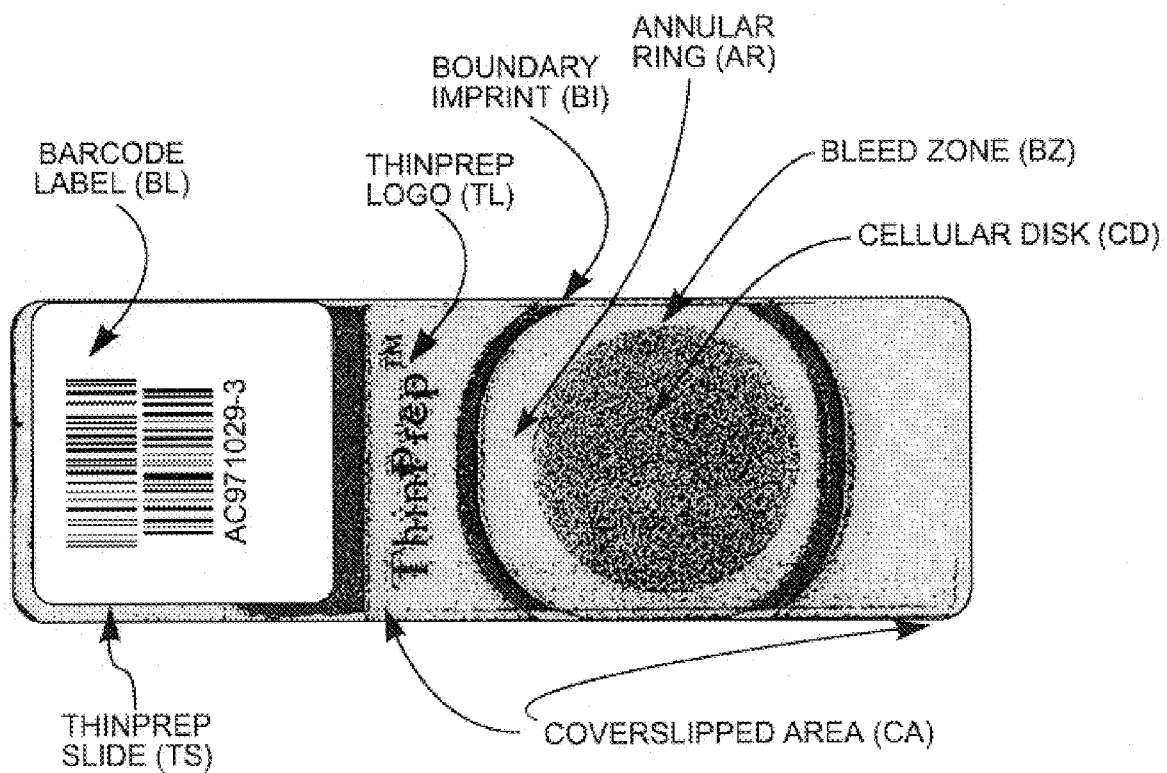
FIG. 9 is a graphical representation of a Cytyc ThinPrep® cervical cytology slide.
Figure 10:
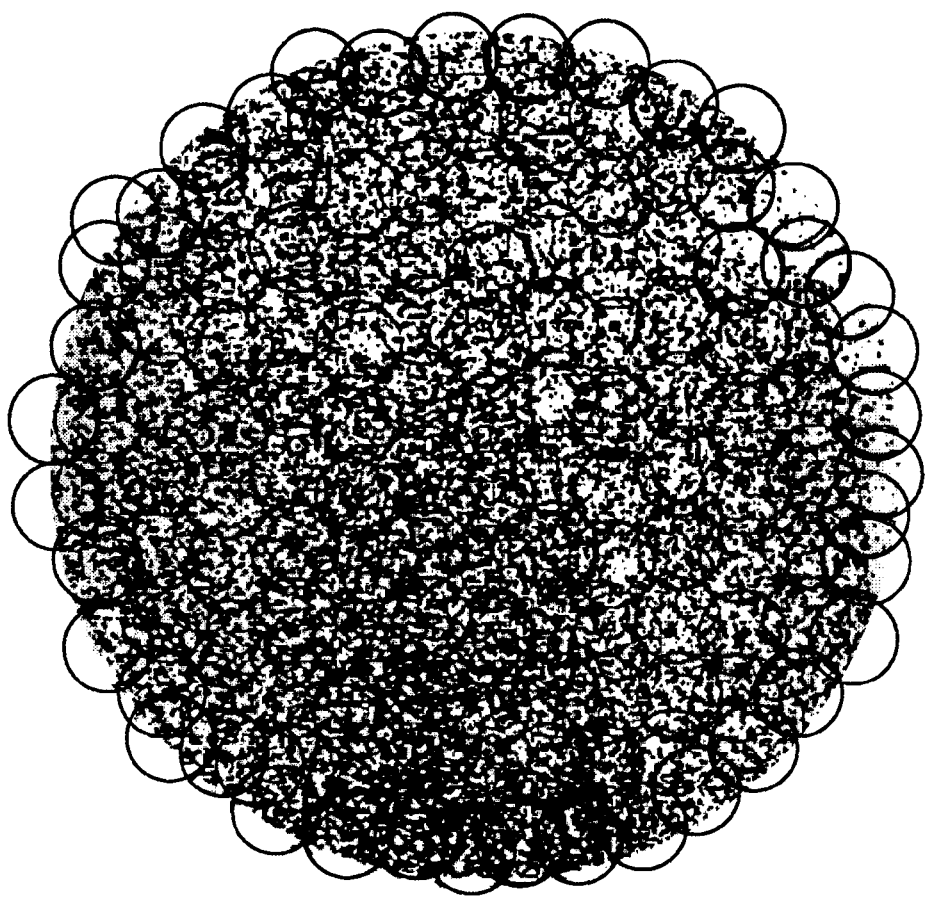
FIG. 10 is an illustration of areas within a cellular disk that are occupied by cells or other light-absorbing objects.

The Cytic ThinPrep® sample preparation thus provides a more spatially uniform distribution of cells within the cellular disk, as shown, for instance, by FIGS. 9 and 10. In the cellular disk of the ThinPrep® slide illustrated in FIG. 10, all objects with an optical density greater than the background peak in the intensity-based frequency histogram are show as black. 100% of the cell deposition area (CD) is covered by presented fields-of-view (FOVs) as determined by a research version of the TRACCELL® system. Note that 26% of the area of the CD is occupied by cells or other light-absorbing objects in the 136 FOVs illustrated by circles.

According to a preferred embodiment of the present invention, after the automated prescreening process, the cytotechnologist conducts a preview of the specimen, at block 24, before actually screening the specimen at block 26. This preview is arranged to channel the cytotechnologist's attention toward significant specimen-related information while allowing the cytotechnologist to focus less on insignificant information or "noise" that does not bear on whether the specimen is normal or abnormal. A object of this preview stage is to minimize the possibility of a false negative diagnosis during the cytotechnologists subsequent screening, by biasing the cytotechnologists attention toward diagnostically significant information. An additional object of this preview stage is to enable the cytotechnologist to more readily compile relevant information about the specimen for review by a diagnosing pathologist in relation to specific areas of the specimen.

As shown in FIG. 9, the area of a ThinPrep® slide on which the cells are transferred is surrounded by a large annular ring, which defines the area to be screened by the cytotechnologist. In the past, a cytotechnologist would have to analyze everything within this ring. The present invention, however, beneficially focuses the cytotechnologist's attention on the relatively small number of diagnostically significant cells actually present in the ring and may thus reduce the time required to screen the specimen.

In this regard, the geometry of monolayer preparations such ThinPrep® slides contain areas of high cellularlity (such as the cellular disk shown in FIG. 10), areas of medium cellularity (e.g., bleed zone), areas of low cellularity (e.g., annular ring), and areas with ultra-low cellularity (e.g., outside the boundary imprint). This a priori contextual information regarding the distribution of cellular material in these liquid-based preparations is exploited by the present invention.

As will be described in greater detail below, the present invention searches for and analyzes sample areas, using this a priori information about the spatial distribution properties of the cells on the slides, before a human cytotechnologist screens the slide. Thus, the present invention can find the most atypical or suspicious cells on the slide, such as those in the fields-of-view illustrated by FIG. 11, and present those areas to the observer, first. Then, the present invention can guide the observer through the remaining fields-of-view with the other (less suspicious) cellular material. This stratified approach enables the screener to review the cellular material on a liquid-based preparation in a sequence such that the most abnormal cells are likely to be encountered earlier in the screening process. This will provide confidence to the observer that they may increase their screening speed, for example, after they initially review fields-of-view with no abnormal cellular material.

During the preview stage 24, the invention beneficially provides the cytotechnologist with a variety of useful information for consideration by the cytotechnologist. This information may be provided to the cytotechnologist in any convenient fashion and in any form. Generally speaking, the invention may include a preview processor to perform this task. The preview processor or "preprocessor" may take the form of a file server, providing an electronic gateway to relevant information about specimens. The file server may store some or all information pertinent to specimens being screened at a given cytology lab or at a remote lab and may serve multiple "client" preview workstations at which pertinent data is displayed. In one embodiment of the invention, the preprocessing functions may be performed by software routines executed by the same computer processor that performs prescreening functions such as mapping. Additionally, the preview display workstations may be incorporated in the same units that are used as the screening stations, such as the ACCELL® workstations.

Whether configured as a standalone unit or incorporated as part of the screening workstation, the preview workstation contemplated by the present invention preferably includes at least one computer or video display, or other mechanism for conveying to an observer pertinent information about a specimen. The workstation is human controlled, providing mechanisms to enable the cytotechnologist to flag information displayed in the preview stage that appears to be particularly pertinent. As the cytotechnologist reviews the preview information, for instance, he or she may operate a mouse or other selection device at the preview workstation, to flag pieces of information that appear to bear on whether the specimen at issue is normal, suspicious, or abnormal. As the cytotechnologist flags pieces of information, or as the preprocessor generates pertinent information about the specimen at issue as will be described below, the information may be automatically appended to the electronic database record associated with the specimen, for convenient review by the pathologist.

Additionally, the workstation preferably includes a bar code reader and mechanism for scanning a bar code or other indicia, to provide a cytotechnologist with preview data associated with a particular specimen. For this purpose, in the event the preview workstation is incorporated as part of the screening station such as the ACCELL® station discussed above, the bar code reader 221 of the ACCELL® screening station may serve to initiate a preview of data pertinent to the specimen under analysis by reading a bar code affixed to the specimen slide.

In use, the preprocessor may obtain a portion of its preview information from external sources such as external databases or direct data entry, and the preprocessor may generate other preview information based on its direct analysis of the specimen at issue. Regardless of its origin, some or all of this information may be displayed for viewing by the cytotechnologist during the preview stage, in order to bias the cytotechnologist's attention toward more diagnostically significant aspects of the specimen. Therefore, all of this information may be referred to as "biasing-information."

Figure 5A:
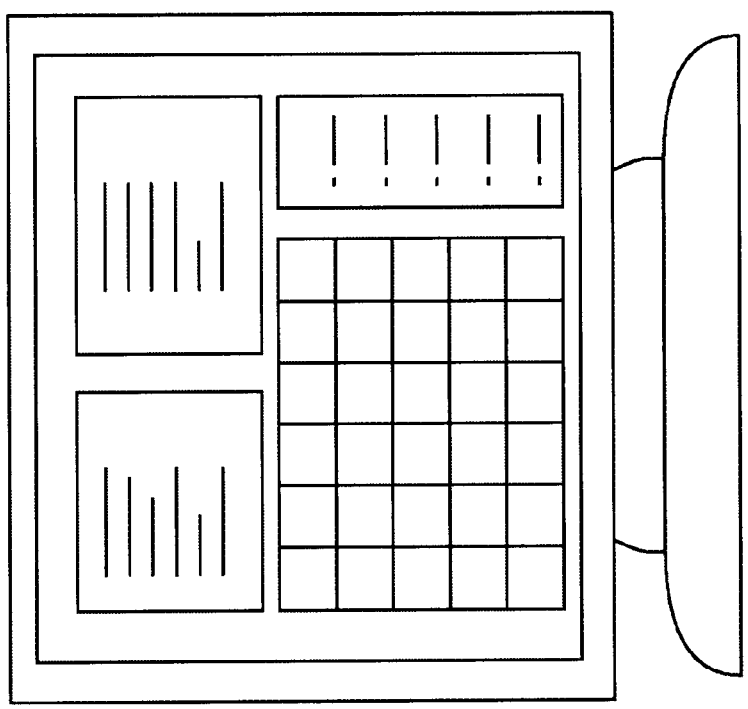
FIGS. 5a and 5b are illustrations of multiple information windows displayed in preview monitor in accordance with a preferred embodiment of the present invention.

As examples, and without limitation, the biasing-information provided to the cytotechnologist by the invention may fall into categories such as (i) images of the specimen, (ii) patient information, (iii) current or previous test results, and (iv) the slide at issue, each of which will be described in more detail below. This information may be selectively displayed in a single window on the preview display or may, alternatively, be displayed in multiple windows for consideration in combination by the cytotechnologist, as depicted, for instance, in FIGS. 5a and 5b. Further, this information may take any of a variety of formats, including, for instance, narrative descriptions, tables, charts, plots, digitized (electronic) images, and microscope fields-of-view, as well as comparison displays of combinations of these data types.

In the preferred embodiment, before displaying the biasing information regarding the specimen at issue, the preprocessor conducts automated image analysis of the specimen. The preprocessor employs the image capture apparatus and performs many of the image processing functions as described above, such as identifying regions of the specimen that contain cellular material, and signaling specimens that are inadequate for testing. In addition, the preprocessor performs functions designed specifically to identify and enable preview display of specimen regions that are likely to be of interest to the cytotechnologist. To do so, the preprocessor preferably analyzes the stored digital images of specimen regions, in search of fields-of-view that contain problematic cells. Region-by-region, the preprocessor builds a buffer identifying and depicting specific cells or clusters of cells in the specimen, in descending order of concern or interest.

More particularly, the preprocessor serially scans through each digitized image in search of images having cellular features that fall within a designated range suggesting a likelihood that the specimen area is of interest. These features may include, for example, specified size, shape, color, optical density (gray level range), texture, and topology (architecture relative to other cells) and combinations of such parameters. Additionally, the preprocessor may also consider other factors pertinent to determining whether given regions of the specimen are likely to be of interest. These factors may include, for instance, data regarding patient medical history and demographics, such as an indication that the patient from whom the sample was drawn is particularly at risk for cancer or other diseases. Such information may automatically signal to the preprocessor that certain cell or field-of-view images that would otherwise be of little interest to a cytotechnologist may be more likely to be of interest. Therefore, the preprocessor may adjust the level of likelihood that various regions of the specimen are of interest, based on such information.

Based on its automated analysis of these parameters, the preprocessor computes an atypicality and complexity index for each image and/or each field-of-view. The preprocessor then stores in a buffer indications of cell or field-of-view locations associated with cells or fields-of-view having varying levels of potential atypicality or complexity, preferably in descending order of atypicality or complexity. In addition, the preprocessor may compute and store an indication of its level of confidence in its probability estimate, such as, for instance, an indication that it is 80% certain that an area of is of interest (e.g., atypical or complex), or that it is only 20% confident in its finding.

Figure 11:
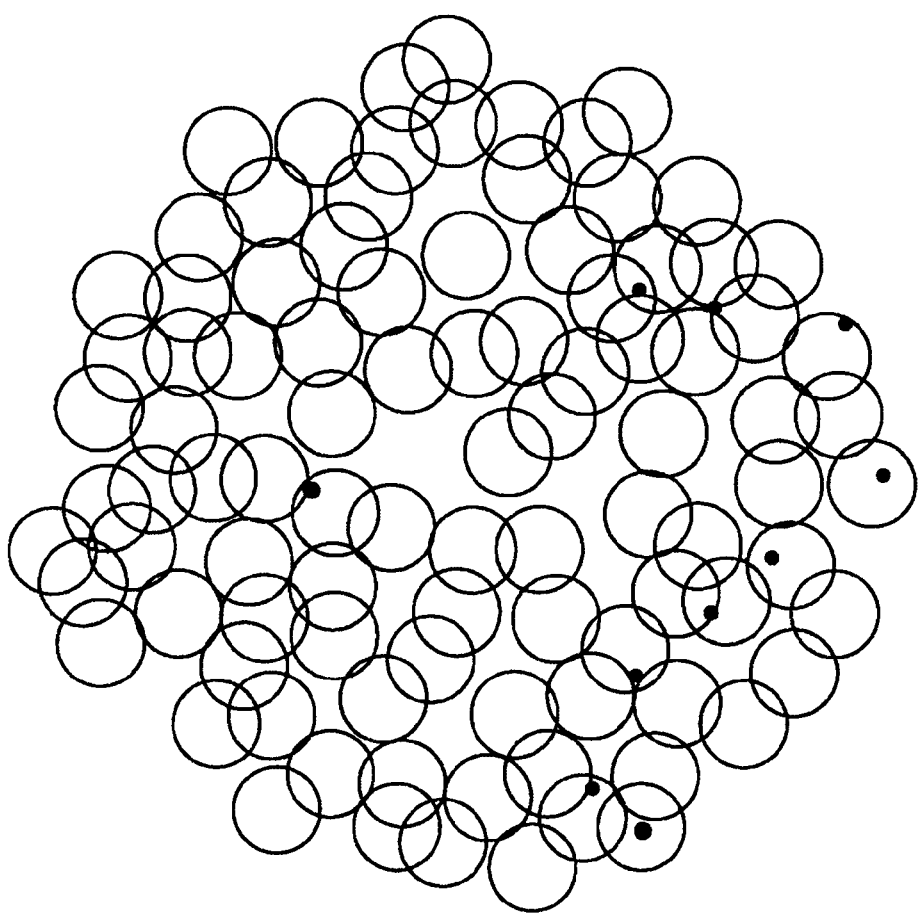
FIG. 11 is a graphical representation showing coordinates and fields-of-view within a ThinPrep® cellular disk that identify suspicious cellular material.

Comparing FIGS. 10 and 11, for example, FIG. 11 shows circular fields-of-view that are to be presented to an operator because they contain material that could not be definitively recognized as either cellular or irrelevant material based upon multi-parameter pattern recognition techniques. The most highly suspicious (e.g., atypical and/or cancer cells) cellular material is marked by an enlarged and dense black dot in this figure. Note that only 95 FOVs remain to be presented to the human cytotechnologist screener in this case.

In the preferred embodiment, the preprocessor also isolates each image of an atypical or suspicious cell or field-of-view apart from any background images, to facilitate preview display of the diagnostically significant images. For instance, the preprocessor may identify the location of a cell or field-of-view in a given digital image and, through automated image processing, eliminate the background around the area of interest and enhance the edges of the cell or field-of-view imager. Alternatively, the preprocessor may shade the background area, in order to usefully retain a visual context of the cell or field-of-view while highlighting the area specifically of interest. This process may require one or more passes through the stored digital images of the specimen.

In addition, the preprocessor may perform other functions to enhance the preview stage. For instance, the preprocessor may be configured to automatically flag certain pieces of information as likely to be pertinent. For instance, the preprocessor may be configured to identify specimens that may be inadequate for one reason or another, such as due to questionable collection, fixation or staining. Rather than rejecting such specimens outright, the preprocessor may set a flag indicating that collection may have been inadequate. As another example, the preprocessor may be configured to identify clusters of cells in the specimen and to flag such areas of the specimen as likely to be pertinent in the cytotechnologist's analysis.

Figure 5B:
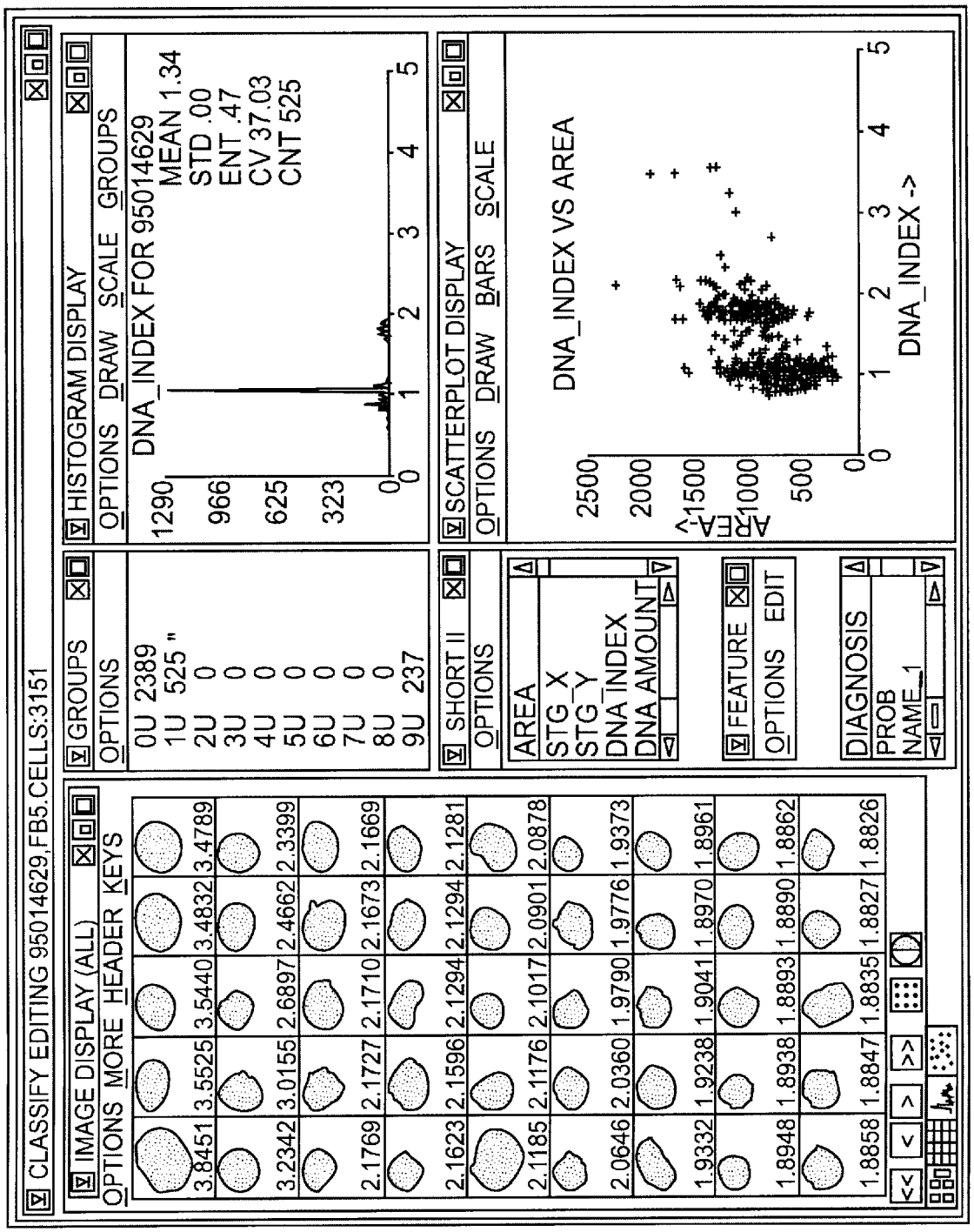
Figures 6, 7:
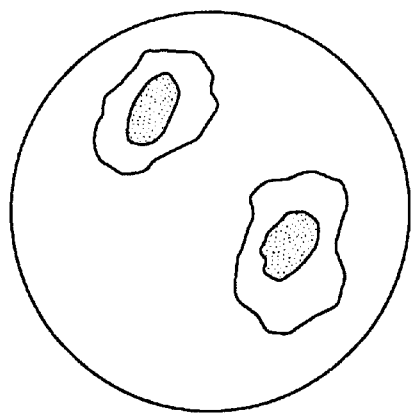
FIG. 6 is an illustration of discrete cell images as displayed in a preferred embodiment of the present invention.
FIG. 7 is an illustration of a microscope field-of-view containing cellular matter of interest within a preferred embodiment of the present invention.

Once the preprocessor has completed its initial processing of the specimen images and data pertinent to the specimen under analysis, the preview workstation displays biasing-information for viewing by the cytotechnologist. As indicated above, one category of such information may be images of the specimen. In this regard, the preprocessor preferably displays at the preview workstation a discrete set of the apparently "most atypical," "most suspect," or "most complex" regions (cells or fields-of-view) for consideration by the cytotechnologist. As depicted in FIGS. 5 and 6, for example, the preprocessor may display a grid of a predetermined number of the most suspect objects or fields. These images may depict either the individual cells or fields-of-view with background images removed or shaded as discussed above. Additionally, the preprocessor may highlight some of the images in this grid (for instance, with color or shading) based on the preprocessor's automated findings, so as to focus the cytotechnologist's attention on particular matters. Similarly, in a preferred embodiment, the preprocessor may display in conjunction with various discrete images, or in relation to the specimen as a whole, a graphical scale or text indicating the preprocessor's degree of confidence in its findings that particular aspects of the specimen are likely to be of interest.

In the event the cytotechnologist identifies any of these discrete objects as suspicious, the cytotechnologist may flag the object, for instance, by clicking a mouse pointer on the discrete image. The operator may further choose to move the specimen physically under manual or computer control to visually review the flagged objects. In a preferred embodiment, the cytotechnologist may also request the preprocessor to specifically characterize a particular cell. Additionally, the cytotechnologist may manually or automatically input into the specimen record notes or associated information keyed to the discrete cell image, for later review by the diagnosing expert.

As an additional convenience, as the cytotechnologist is examining these discrete cell or field-of-view images, the cytotechnologist may click on or otherwise select any of these images in order to see an actual microscopic field-of-view or a magnified digital image of the specimen area that includes the cell, as illustrated for instance by FIG. 7. To provide this function, the preprocessor may communicate with the specimen-mapping system (such as the TRAC-CELL® system) to direct the screening station (such as the ACCELL® screening station) to display the associated field-of-view. Alternatively or additionally, this actual microscopic field-of-view may be displayed directly on the same monitor that serves as the preview display. In this way, the cytotechnologist may quickly view the actual context of any cell that the cytotechnologist sees as possibly suspect.

In addition, as suggested above, the preprocessor displays for preview by the cytotechnologist a series of other pertinent biasing-information, obtained by the preprocessor from external data sources and/or based on its own automated analysis. This information may be displayed on the same or a different display than the discrete images of the cells or fields-of-view. In the preferred embodiment, however, this information is displayed on the same display as the discrete specimen images, so that the cytotechnologist can consider the other information in the context of the specimen images.

One area of biasing information may relate to the patient from whom the sample was drawn and may include, for example, epidimiologic risk factors and abnormal prior physical examinations or laboratory test results. Employing the preview system of the present invention in the context of a lung cancer test, rather than a cervical Pap smear test, for example, the preprocessor may usefully display an indication of the number of packs of cigarettes per year that the patient has smoked. If the patient has smoked more than a designated number of pack-years, for instance, the technician may wish to flag this information, as the information may bear significantly on whether or not the specimen is at high risk to be abnormal. As another example, in the context of a Pap smear test, information about abnormal prior test results may include the results of cellular DNA tests previously conducted on patient specimens. Still additionally, patient information may include, for example, other patient medical records, family medical history, and patient demographics. For instance, this information may include specific patient risk factors for particular diseases based on family history data.

Another area of biasing-information may relate to the results of other tests that have been conducted on the same specimen being analyzed, for instance, from samples derived from aliquots of the same specimen, possibly included on a discrete area of the same slide. As an example, if the specimen has undergone an HPV or a cellular DNA Ploidy test by the cytology laboratory conducting the Pap smear screening, the results of this test may be usefully displayed at the preview workstation for convenient examination by the cytotechnologist. FIG. 5b shows an example of a computer display of a discrete set of nucleus images that appear to be of most interest in a given specimen, together with a DNA histogram and scatterplot display for the same specimen.

Still a further area of biasing-information may relate to the slide at issue. This information may include information flagged or noted by the preprocessor based on its analysis of the specimen images. For instance, the preprocessor may include on the preview display an indication that a given area of the specimen contains a cell cluster and is therefore more likely to be of interest. Information related to the slide at issue may also concern how the slide has been handled or mishandled in the cytology screening lab or whether the specimen is adequate in accordance with standards such as the Bethesda Classification Code for gynecological specimens. In this regard, pertinent information may concern specimen collection, fixation and/or staining.

With regard to specimen collection, for example, the sample that was drawn from the patient may contain an inadequate vaginal, cervical or endocervical component. Alternatively, the specimen may contain an inadequate number of cells and therefore be viewed as insufficient. To make these determinations, the preprocessor may automatically analyze the stored digital images of the specimen to determine whether the specimen lacks cells that would be expected to be present in complete samples.

With regard to specimen fixation, those of ordinary skill in the art appreciate that a sample taken for a Pap smear test must typically be dipped into or sprayed with alcohol immediately after being drawn, in order to preserve the sample. If the sample is not properly dipped into or sprayed with alcohol, air drying may rupture the nuclear envelope or alter the chromatin structure, creating a blurry effect on the Pap smear slide and decreasing the diagnostic value of the sample. The preprocessor system may be arranged to analyze automatically the stored digital images of the specimen to identify the presence of drying artifacts, which would reflect inadequate fixation.

With regard to staining, the preprocessor may employ automated digital image analysis techniques to determine that the specimen was overstained or understained in that it was subjected to too much or too little hematoxylin. Alternatively, the system may determine that the specimen was understained in that it was not subjected to enough hematoxylin. In either case, the preprocessor may display for examination by the cytotechnologist information identifying the adequacy of staining. The operator may flag such information and thus determine that the specimen at issue should not undergo an accelerated screening process.

By displaying information about inadequate collection, fixation or staining, the cytotechnologist may conveniently identify and note inadequate specimens and may flag the significant information for pathologist review. Additionally, in the event the cytotechnologist determines, based on this information, that the specimen at issue is inadequate, he or she may either tag the specimen to be returned without further analysis or immediately forward the specimen to the expert pathologist for diagnosis.

Still further, as the cytotechnologist is examining the biasing-information displayed at the preview workstation, and particularly as he or she is previewing the grid of discrete cell or field-of-view images, the preprocessor preferably provides the cytotechnologist with access to a referential database to help analyze and place the specimen in context. The preprocessor may include or may be locally or remotely interconnected to a database containing information about other specimens. This database may associate particular cellular characteristics with certain circumstantial information similar to the information provided to the cytotechnologist for preview. As the cytotechnologist notes a discrete specimen image of interest, the cytotechnologist may query the relational database for information about other similar cells, or the preprocessor may be arranged to automatically display pertinent information from the database. In doing so, the preprocessor may conveniently form a search filter based on the information currently flagged by the cytotechnologist. The preprocessor may thereby efficiently obtain database information about similar cells with similar background information.

During the preview process, the preprocessor and human technician interact and learn from each other, each gaining additional information that may aid in the cytotechnologist's subsequent screening of the specimen and perhaps ultimately in a pathologist's diagnosis. Principally, the cytotechnologist benefits from viewing the biasing-information displayed by the preprocessor, because this information enables the cytotechnologist to focus attention on diagnostically significant aspects of the specimen. As a result, if the cytotechnologist has not detected or flagged anything suspicious or noteworthy about the specimen after examining the information provided by the preview preprocessor, then the cytotechnologist does not need to spend a significant amount of time looking at the slide. The cytotechnologist may instead assume that the specimen is probably one of the 90% to 95% that are normal, and the cytotechnologist may quickly screen the slide for any cellular abnormalities. Alternatively, if the cytotechnologist detects some possible abnormalities during this prescreening process or has flagged information that may suggest the presence of abnormalities, then the cytotechnologist may properly spend more than an average amount of time screening this potentially abnormal case. In this way, the present invention beneficially channels the cytotechnologist's attention during actual screening on specimens that are most likely to be suspicious or abnormal. On the other hand, the invention enables the cytotechnologist to avoid spending unnecessary excess time screening specimens that are likely to be within normal limits.

In addition, the preprocessor may learn significant information about the specimen at issue from actions or behavior of the cytotechnologist, and the preprocessor may use this information—in addition to other information that it gleans from the specimen and/or from external data—to prepare for efficient screening by the cytotechnologist. At one level, for instance, this information may be as simple as the fact that the cytotechnologist requested an exploded view of a specific specimen region or requested referential database information in comparison to a specific specimen region. Knowing that the cytotechnologist took such action regarding the specific specimen region may signal to the preprocessor that the region is of significance to the cytotechnologist.

At another level, the preprocessor may acquire information about potentially significant areas of the specimen at issue by monitoring the behavioral patterns of the cytotechnologist during the preview process. In this regard, it has been determined that some of the reactions of the cytotechnologist, even if subconscious, may convey information about significant aspects of the specimen at issue. These cytotechnologist reactions may include, for instance, the movement patterns of the cytotechnologist's eyes viewing the preview screen, the amount of time that the cytotechnologist's eyes focussed on particular pieces of biasing-information, and the cytotechnologist's pupil dilation. As an example, if the cytotechnologists eyes suddenly move to or focus on a particular image of a specimen region, the region of new focus may be a diagnostically significant area of the specimen.

In a preferred embodiment of the present invention, based on the information that the preprocessor gleans from its automated preprocessing as well as during the preview by the cytotechnologist, the preprocessor next generates a routing function to facilitate automated microscopic display of a portion of the specimen at the screening station. As described above, such a routing function, or routing pattern, is keyed to the spatial coordinates on the specimen slide that were recorded during prescreening. In the preferred embodiment, the preprocessor may base the routing pattern on any of a variety of criteria. Such criteria may include, for example, the descending order of atypicality or complexity previously established, the regions that the cytotechnologist flagged as being of interest during preview, and/or the regions that the preprocessor determined to be suspicious such as those regions that contain fragments or that are overstained or understained.

Additionally, the preprocessor may configure the routing pattern for most efficient physical display at the screening station. As those of ordinary skill in the art will appreciate, microscopically displaying regions of a specimen in an order based on level of interest could result in inefficient movement around the slide from one region to another. To avoid this result, the preprocessor may configure the routing function to group specimen regions first by level of interest and then by location on the slide. For instance, assuming the preprocessor has selected 100 regions that appear to be most likely to be "most atypical," "most suspect," or "most complex," the preprocessor may order the top 25 of those regions by location, the next 25 by location, and so forth. In this way, the screening station will require less movement about the slide to enable screening of the portion of regions designated by the preprocessor.

Provided with the biasing-information from the preview stage, the cytotechnologist next conducts actual screening of the specimen. At this stage, the screening station displays microscopic views of a portion of the specimen according to the routing function developed by the preprocessor and at a most efficient rate. However, ultimate control over the manner of display, such as speed and route, remains in the hands of the cytotechnologist, for instance through a control panel, keyboard or other input device provided at the screening station.

In a preferred embodiment, for instance, the routing function may call for the screening station to microscopically display regions of the specimen in descending order of probability that the regions are of interest. Recognizing that probabilities of interest are likely to diverge more between the specimen regions that are more "atypical," "suspect" or "complex" than those that are ranked lower by the preprocessor, the screening station may be preset to route more quickly through regions with higher probabilities and slower through other regions. The increase in speed as less interesting regions are displayed for screening may be continuous throughout the screening process. Alternatively, the screening station may, for instance, display a first group of specimen regions at one rate and then another group of regions at another rate. Notwithstanding the automated display in accordance with the routing function, however, the cytotechnologist may at any time elect to stop or manually alter the screening process.

Similarly, recognizing that the cytotechnologist is likely to be more interested in those specimen regions ranked with higher levels of suspicion by the preprocessor, the screening station may be set to display for a minimum period of time regions of the specimen regions that have been determined to have at a predetermined interest level. For instance, the screening station may be set to display for at least 5 seconds each of the top 10 "most atypical," "most suspect," or "most complex" specimen regions. The screening station may then display other specimen regions relatively more quickly, again always allowing the cytotechnologist to interrupt the automated screening process and proceed manually.

The cytotechnologist may also, or alternatively, set the screening station to route through areas of the specimen in a desired order or at a desired rate. For instance, the cytotechnologist may set the screening station to highlight or stop the screening process at each field-of-view that contains one of the "most atypical," "most suspect," or "most complex" cells, objects, or fields-of-view that was displayed during the preview stage. In this way, the cytotechnologist may automatically see these specimen regions in context. As another example, the cytotechnologist may conveniently set the screening workstation to stop automatically at every field-of-view containing one or more of the suspicious cells or at each complex or otherwise flagged field-of-view. Still additionally, the cytotechnologist may set the screening station to stop at only those "most suspicious" cells that the cytotechnologist flagged during the preview stage or to stop at only those fields-of-view that meet specified criteria, such as those containing fragments or those that were understained or overstained. Of course, as those of ordinary skill in the art will appreciate, the screening station may alternatively be prearranged to automatically route through one or more of these fields-of-view with or without direct input from the cytotechnologist.

As still another variation, the screening station may be preset or configured by input from the cytotechnologist with a maximum total screening time. Provided with the routing function developed by the preprocessor, for instance, the screening station can then display specimen regions at a rate designed to not exceed the preset maximum time. Again, however, the cytotechnologist is preferably provided with the ability to interrupt such automated screening at any time, or to proceed with automated screening without the maximum time constraint.

The present invention further contemplates that information gleaned during the preview stage may be presented to the cytotechnologist during the screening stage, in conjunction with specimen images being screened. For instance, the screening station may display pertinent information about a given field-of-view on a monitor as text or graphics next to the actual field-of-view or overlapped over the field of view. Additionally, the screening station may display a sliding bar scale indicating the preprocessor's degree of confidence in ranking of probability of interest, similar to that described above in the context of the preview stage.

Finally, as in the preview stage, the present invention contemplates monitoring the actions or behavior of the cytotechnologist during the screening stage. As described above, these actions or behavior may include, for example, the movement of the cytotechnologist's eyes or the dilation of the cytotechnologist's pupils.

Information gleaned from these behavioral patterns may be subsequently provided to the cytotechnologist's supervisor or other expert for review. In this way, the expert may review not only those specimen regions consciously identified by the cytotechnologist as problematic but also those regions that the cytotechnologist subconsciously deemed to be most important. As a result, the analysis of the specimen is rendered more efficient.

Still further, recording information gleaned from a cytotechnologist's behavioral patterns, such as points of focus or times of focus, may offer additional benefits related to specimen analysis. For instance, the information may be used for quality assurance, or for training, education and proficiency testing reviews of cytotechnologists. Further, such information may facilitate a variety of pre-emptive actions in response to the conditions or behavior of the observer. As a general example, an indication that an observer is shivering may signal a need to increase heat.

Preferred embodiments of the present invention have been illustrated and described. It will be understood, however, that changes and modifications may be made to the invention without deviating from the spirit and scope of the invention, as defined by the following claims.

For instance, the present invention is not limited to use in connection with Pap smear screening, but may extend to other specimen inspection processes. In this regard, it will be appreciated that other specimen preparation methods and instruments may give rise to different a priori information that may be previewed by an observer in accordance with the present invention.

The invention is also not limited to use in connection with automated screening systems such as the TRACCELL® mapper and the ACCELL® screening station. The invention may extend to manual specimen screening systems, whether or not guided by established microscope routing patterns.

What is claimed is:

1. A method for assisting an observer to analyze a specimen, said specimen defining a plurality of regions, said method comprising, in order, the following steps:

acquiring into a machine a set of data regarding a plurality of said regions;

displaying for preview by said observer a set of biasing-information including a first subset of said regions defined according to a probability estimate that said regions are of interest, whereby subsequent screening of said specimen by said observer may be biased by said observer's preview of said biasing-information;

displaying for screening by said observer a second subset of said regions; and ranking a plurality of said regions according to level of likelihood that said regions are of interest, wherein ranking said plurality of regions comprises automatically performing the following steps:

detecting objects within one or more of said plurality of regions;

categorizing each of said objects as being either a cellular object or a non-cellular object, wherein each cellular object has at least one cellular characteristic;

classifying each cellular object at least in part according to said at least one cellular characteristic, and interpreting each cellular object as being either a normal cellular object or an abnormal cellular object, based at least in part on medical information specific to said patient.

2. A method as claimed in claim 1 wherein said cellular characteristic is selected from the group consisting of size, shape, color, optical density, texture and topology.

3. A method for assisting an observer to analyze a specimen, said specimen defining a plurality of regions, said method comprising, in combination, the following steps:

acquiring into a machine a set of data regarding a plurality of said regions;

conducting a comparison between at least one cellular characteristic observed in said regions and a corresponding reference cellular characteristic;

assigning a level of significance to said comparison at least in part based on information selected from the group consisting of medical history of said patient and demographics of said patient;

based on said comparison and said level of significance, automatically establishing a probability estimate that said regions are of interest;

displaying for preview by said observer a set of biasing-information including a first subset of said regions defined according to said probability estimate that said regions are of interest, whereby subsequent screening of said specimen by said observer may be biased by said observer's preview of said biasing-information; and displaying for screening by said observer a second subset of said regions.

4. A method as claimed in claim 3, wherein establishing said probability estimate comprises automatically performing the following method steps:

detecting objects within one or more of said plurality of regions;

categorizing each of said objects as being either a cellular object or a non-cellular object, wherein each cellular object has at least one cellular characteristic;

classifying each cellular object at least in part according to said at least one cellular characteristic, and interpreting each cellular object as being either a normal cellular object or an abnormal cellular object, based at least in part on information specific to said patient.

5. A method as claimed in claim 4 wherein said method steps are performed by a computer operating software.

6. A method as claimed in claim 4 wherein said information specific to said patient comprises a medical history of said patient.

7. A method as claimed in claim 4 wherein said information specific to said patient comprises demographics of said patient.

8. A method as claimed in claim 4 wherein interpreting each cellular object as being a normal cellular object or an abnormal cellular object comprises conducting a weighted comparison between said at least one cellular characteristic and at least one reference cellular characteristic, wherein greater or lesser weight is assigned to one or more of said at least one cellular characteristic depending on said information specific to said patient.

9. A method as claimed in claim 8, wherein said at least one reference cellular characteristic is derived from classified cellular objects associated with said specimen.

10. A method as claimed in claim 8, wherein said information specific to said patient comprises a medical history of said patient.

11. A method as claimed in claim 8, wherein said information specific to said patient comprises demographics of said patient.

12. A method for assisting an observer to analyze a specimen, said specimen defining a plurality of regions, an apparatus receiving a set of data representing said regions, said method comprising the following method steps automatically performed by said apparatus:

analyzing said data and detecting objects within one or more of said regions;

categorizing each of said objects as being either a cellular object or a non-cellular object, wherein each cellular object has at least one cellular characteristic;

classifying each cellular object at least in part according to said at least one cellular characteristic;

conducting a comparison between said at least one cellular characteristic and a corresponding reference cellular characteristic;

assigning a level of significance to said comparison at least in part based on information selected from the group consisting of a medical history of said patient and demographics of said patient;

based on said comparison and said level of significance, establishing a probability estimate that said regions are of interest;

displaying for preview by said observer a set of biasing-information including a first subset of said regions defined according to said probability estimate, whereby subsequent screening of said specimen by said observer may be biased by said observer's preview of said biasing-information; and displaying for screening by said observer a second subset of said regions.

13. A system for assisting an observer to analyze a specimen, said specimen defining a plurality of regions, said system comprising, in combination:

an automated video microscope capturing one or more digitized images of said specimen;

a programmed computer operating a set of instructions for (i) analyzing said digitized images and detecting objects within one or more of said digitized images, (ii) categorizing each of said objects as being either a cellular object or a non-cellular object, wherein each cellular object has at least one cellular characteristic, (iii) classifying said cellular objects at least in part according to said at least one cellular characteristic, (iv) conducting a comparison between said at least one cellular characteristic and a corresponding reference cellular characteristic, (v) assigning a level of significance to said comparison at least in part based on information selected from the group consisting of a medical history of said patient and demographics of said patient; and (vi) based on said comparison and said level of significance, establishing a probability estimate that said regions are of interest;

means for displaying for preview by said observer a set of biasing-information including a first subset of said regions defined according to said probability estimate, whereby subsequent screening of said specimen by said observer may be biased by said observer's preview of said biasing-information; and means for displaying for screening by said observer a second subset of said regions.

\* \* \* \* \*